(12) United States Patent
Nakagawa

(10) Patent No.: US 6,432,910 B2
(45) Date of Patent: Aug. 13, 2002

(54) FIBER TREATING AGENTS AND METHODS OF TREATING FIBERS

(75) Inventor: Momoki Nakagawa, Heim Topaz 2nd Floor, 3-20-4-204, Kyojima, Sumida-ku, Tokyo 131-0046 (JP)

(73) Assignees: Gunze Co., Ltd., Kyoto; Kenji Nakamura, Osaka; Momoki Nakagawa, Tokyo, all of (JP)

( * ) Notice: Subject to any disclaimer, the term of this patent is extended or adjusted under 35 U.S.C. 154(b) by 22 days.

(21) Appl. No.: 09/759,987

(22) Filed: Jan. 12, 2001

(30) Foreign Application Priority Data

Jan. 18, 2000 (JP) .......................... 2000-009117

(51) Int. Cl.⁷ ............................ C11D 1/62; C11D 3/384
(52) U.S. Cl. ................. 510/504; 510/123; 510/308; 510/329; 510/330; 510/463; 428/96; 428/245; 428/260; 428/279
(58) Field of Search ................. 510/123, 308, 510/329, 330, 504, 463; 428/96, 245, 260, 279

(56) References Cited

U.S. PATENT DOCUMENTS 6,362,142 B1 * 3/2002 Weber et al. ............... 510/119

FOREIGN PATENT DOCUMENTS

| EP | 0 761 867 | 3/1997 |
| JP | 63 010715 | 1/1988 |
| JP | 08 060547 | 3/1996 |
| JP | 09 296367 | 11/1997 |
| WO | WO 99/03959 | 1/1999 |

* cited by examiner

*Primary Examiner*—Charles Boyer
(74) *Attorney, Agent, or Firm*—Knobbe, Martens, Olson and Bear, LLP.

(57) ABSTRACT

Fibers are treated with fiber treating solutions comprising an animal protein hydrolysate, chitosan lactate and one or more kinds of quaternary ammonium salts. The fiber treating solutions provide a smooth, soft and supple feel due to a moisture-retaining property and physiological skin protecting effects. Underwear products has physiological skin protecting effects obtained by treating with these fiber treating solutions.

18 Claims, No Drawings

FIBER TREATING AGENTS AND METHODS OF TREATING FIBERS

BACKGROUND OF THE INVENTION

1. Field of the Invention

The present invention relates to agents for treating the surface of fiber products which contact the skin.

The present invention also relates to fiber treating agents which permanently provide physiological skin protecting effects to prevent rough, dry and itchy skin and to improve immunity or the like, and methods for treating fibers using said fiber treating agents.

2. Description of the Related Art

Currently, the incidence of atopic dermatitis is increasing and has become a social problem. Atopic dermatitis is considered to be caused by changes in the housing environment associated with the advanced standard of living, which results in an abnormality in skin barrier function and a decrease in heat-retaining ability of the horny layer.

Deterioration in immunity, which causes atopic dermatitis, is known to be largely affected by eczema or itching caused by irritation of the skin caused by clothes such as underwear. Accordingly, it would be very advantageous if clothes which directly contact the skin can be treated so as to acquire improved skin barrier function and moisture retaining function of the horny layer, and physiological skin protecting effects to improve skin immunity and to suppress skin dryness, roughness and itching. However, no fiber treating agent which provides such effects has been known until now.

Conventionally, collagen is known to be effective for retaining moisture in the skin horny layer. There is a method in which natural collagen particles are dispersed on a urethane resin base to form a membrane to form a material having highly transparent and highly moisture-absorbing/exhaling properties, providing no sticky sweating feeling when worn (Japanese Patent Laid Open, No. H04-82974) and an agent to treat the surface of covering non-woven fabrics for moisture-retaining sanitary products, which is composed of a collagen hydrolysate and a surfactant (Japanese Patent Laid Open, No. S62-90375). However, collagen was found to be inappropriate for use as a fiber treating agent by itself because of its sticky property which resulted in an unsatisfactory feel when used for treating underwear. On the other hand, chitin and chitin derivatives, which are present amply and ubiquitously in nature as a complex with proteins in invertebrate animals, bacteria, fungi or the like, are known to be used as an agent for treating fibers to provide an antimicrobial effect without causing skin damage and to improve water absorbing property and water dispersing property, as well as water proofing property and moisture permeating property (Japanese Patent Laid Open, No. H03-76871). However, the chitin compounds are simply dispersed on the fibers, and as such are dissolved or released from the resulting fiber products upon washing, which results in poor durability.

Furthermore, a technique for graft polymerization of collagen having an excellent absorbing/exhaling property is known to improve a durable antimicrobial property of underwear (Japanese Patent Laid Open, No. H07-300770); however, the technique can be used only for polyester fibers, which impedes its broad applicability. Further, an attempt was made to prepare a fiber treating agent, in which collagen was held with chitosan carboxylate to dissolve the stickiness of collagen and a synthetic resin binder was admixed. However, the use of a binder made it difficult to attain a soft feel and caused considerable skin irritation. Moreover, because of the concealing effect of the binder, it became difficult for the collagen component itself to directly act on the skin and thus physiological protecting effects, the primary object, could not be satisfactorily attained.

Further, the use of fiber treating agents primarily consisting of silk proteins is known. For example, the surface of fibers is treated with silk granules (Japanese Patent Laid Open, No. H08-49161), the hydrophilicity of fibers is improved by treating with sericin (Japanese Patent Laid Open, No. H09-322911), and sericin is applied on the surface of fibers to produce materials for fiber products which have direct contact with skin, such as diapers, eye bandages, facial packs, and wet napkins (Japanese Patent Laid Open, No. H10-1872); however, none of them are satisfactory in terms of comfort to the skin and moisture retention of the horny layer. A technique to fix a mixture of liquid or powder of a protein component extracted from cocoon hydrolysate and a synthetic resin binder onto fibers is also known. However, because of the concealing effect of the binder, it became difficult for the sericin component to act on the skin and thus expected physiological protecting effects could not be satisfactorily attained; skin stimulation became disadvantageously difficult by the use of the binder and the durability of the resulting underwear and towels were not satisfactory when washed repeatedly.

On the other hand, treatments of fibers with a treatment solution containing quaternary ammonium salts are also known, which include a treatment to attain soft feel (Japanese Patent Laid Open, No. H07-82668), a treatment to improve water repelling and oil repelling properties (Japanese Patent Laid Open, No. H07-145119), a treatment to improve an antimicrobial property, deodorizing property, and water absorbing workability (Japanese Patent Laid Open, No. H08-311769), a treatment to prevent static electricity (Japanese Patent Laid Open, No. H09-173961; Japanese Patent Laid Open, No. H10-37071), and a treatment to improve gloss and smoothness (Japanese Patent Laid Open H10-237771). However, none of these provides physiological protecting effects.

Furthermore, a combined use of collagen and chitosan quaternary ammonium salts is also known. For example, collagen and/or an antimicrobial agent are graft-polymerized on the surface of polyester fibers to obtain modified polyester fibers having an excellent antimicrobial property, moisture absorbing/exhaling property and water absorbing property (Japanese Patent Laid Open H7-300770). However, this technique is for producing fiber products having the abovementioned properties on a large scale and not for post processing of fibers. Moreover, the resulting products were not satisfactory in terms of wear feeling and physiological protecting effects as found in fibers obtained according to the present invention.

Conventionally, 1,3-butyleneglycol, sorbitol, hyaluronic acid, CPCM chitosan, or the like are generally used as skin moisture-retaining agents. However, recent studies revealed that natural moisturizing factor (NMF) components have greater effects on the moisture retention of the horny layer and the restoration of the skin barrier function than the abovementioned conventional moisture-retaining compounds.

These natural moisturizing factor components are more effective in preventing eczema, rough and dry skin and itching and improving immunity than conventionally used moisture-retaining agents, and are considered to be excellent components for the restoration of the skin barrier function and the moisture-retention of the horny layer. Many attempts are now under consideration to compound the natural moisturizing factor components into skin medicines for external application.

Major natural moisturizing factor components referred to herein and their percentages are shown in Table 1.

Table 1 Percentages of natural moisturizing factor components (% by weight)

TABLE 1

Percentages of natural moisturizing factor components (% by weight)

| | |
|---|---|
| Amino acids | 40.0% |
| Pyrrolidonecarboxylic acid | 12.0 |
| Lactates | 12.0 |
| Glucosamine | 1.5 |
| Na, Ca, Mg, K, PO$_4$ | 18.5 |
| Peptides and the like | 8.5 |
| Urea | 7.0 |

SUMMARY OF THE INVENTION

An objective of the present invention is to restore the skin barrier function and to improve the moisture-retaining function of the horny layer by fixing large percentages of the abovementioned natural moisturizing factor components, but not moisture-retaining agents which are conventionally used for cosmetics or the like, onto fibers.

The present invention can provide underwear having a gentle and soft feel to the skin and protective effects by fixing the natural moisturizing factor components onto fibers without having to use a synthetic resin binder, if possible.

In the present invention, as for the natural moisturizing factor components, an animal protein hydrolysate or an extract extracted from animal dermal bones is used as amino acids and peptides, chitosan is used as glucosamine, chitosan lactate is used as a lactate, and Na, etc. can be included by the neutralization with an alkaline of the acid used for the protein hydrolysis. About 80% of the natural moisturizing factor components can be fixed onto fibers by applying a treating agent composed of these components, without using a synthetic resin binder.

Namely, the present invention is primarily composed of a fiber treating solution containing an animal protein hydrolysate, chitosan, a lactate, and one or more kinds of quaternary ammonium salts to improve physiological skin protecting effects by fixing the natural moisturizing factor components onto clothes, and a method of treating fibers by using this fiber treating solution.

A fiber treating solution according to the present invention primarily comprises amino acids, peptides, lactates, glucosamine, and Na, etc., which are composed of about 40%, about 8.5%, about 12%, about 1.5%, and about 18.5% of natural moisturizing factor components, respectively, and in terms of preventing decomposition of protein hydrolysates and undesirable bacterial growth on the surface of fibers, its antimicrobial activity can be maintained without using any paraben bactericidal agent. The use of such fiber treating agent of the present invention provides a material exhibiting less irritation to the skin, and resulting underwear have favorable soft and smooth feel and excellent physiological skin protecting effects to prevent skin dryness, roughness and itching and to improve immunity and the like.

As an animal protein hydrolysate in the present invention, natural collagen extracted from animal dermal bones, an extract of atherocollagen hydrolysate having a molecular weight of 5,000 to 100,000, or an extract of sericin or fibroin hydrolysate having a molecular weight of 5,000 to 100,000 is used. For example, sericin can be obtained by treating silk with hydrochloric acid at 50 C. for about 1 to 2 hours to attain a molecular weight of about 5,000 to 100,000, neutralizing with sodium hydroxide, and then filtering through an active carbon layer or an ultrafiltration membrane to obtain a filtrate.

The filtrate contains a component at a concentration of about 0.2% and can be concentrated for use, if necessary. The use of sericin is effective as an antipollution measure since sericin removed from silk conventionally goes into waste and pollutes the natural environment. Fibroin can also be obtained from silk simultaneously by hydrolysis to attain a molecular weight of 5,000 to 100,000. An animal protein hydrolysate extract having a molecular weight of 5,000 to 100,000 is preferable because the moisture-retaining effect of the horny layer and the skin barrier effect decline when the molecular weight of the extract is greater than 100,000.

In the present invention, an animal protein hydrolysate is incorporated with chitosan lactate by heating a mixture of the animal protein hydrolysate and the chitosan lactate.

The material thus obtained is gelled by drying and forms a membrane on the surface of fibers treated therewith, but this gel membrane by itself does not adhere to the fibers and is not durable to washing. However, washing durability is greatly improved by using a specified quaternary ammonium salt as an additional component, as described later.

In the present invention, the abovementioned lactic acid is effectively used as a natural moisturizing factor component. Pyrrolidonecarboxylic acid can also be used, but acids such as acetic acid, malic acid and formic acid are not preferable.

In the present invention, an animal protein hydrolysate and quaternary ammonium salts are mixed and heated so that the animal protein hydrolysate is incorporated with the quaternary ammonium salts. The resulting product differs as a function of the molecular weight of the quaternary ammonium salts used; of guanidine ammonium salts, trimethyl ammonium salts are most effective to fix chitosan lactate. Furthermore, quaternary ammonium salts used in the present invention not only incorporate and fix a protein hydrolysate onto fibers but also have a function to fix the gel membrane of chitosan lactate and the protein hydrolysate onto fibers. Thus, quaternary ammonium salts selected from alkyl trimethylammonium salts, betaine ammonium salts, and guanidine ammonium salts can impart washing durable absorbability, softness, smoothness, and antimicrobial property to underwear.

Of the abovementioned quaternary ammonium salts, alkyl trimethylammonium salts having dodecyl, palmalkyl, hexadecyl, lauryl, myristyl, cetyl, stearyl, or oleyl as the alkyl group are preferably used. Further, trimethyl glycine can be used as a betaine ammonium salt. Betaine ammonium salts are adhesive to fibers, and are notably soft and smooth, and can be used as hair rinsing agents because they are safe for human use. Further, triethyoxysilylpropyl grafted polyhexamethyleneguanidine hydrochloride (YBS-TX, a product of SK Co., Ltd, Korea) is effectively used as a guanidine ammonium salt.

Further, some of the abovementioned quaternary ammonium salts cause rashes or rough and dry skin; any salts other than those mentioned above can be used in the present invention as long as they are gentle to the skin.

DETAILED DESCRIPTION OF THE PREFERRED EMBODIMENT

The present invention is to fix skin natural moisturizing factor components onto fibers for clothes by treating said fibers with a fiber treating solution comprising an animal protein hydrolysate, chitosan lactate, and one or more kinds of quaternary ammonium salts.

Namely, in the present invention, one part of animal protein hydrolysate and 1 to 3 parts of chitosan lactate are mixed and stirred at 20 C. for 2 hours to obtain solution A. Separately, one part of animal protein hydrolysate and 1 to 3 parts of quaternary ammonium salts selected from alkyl trimethyl type, betaine type, and guanidine type ammonium salts are mixed and stirred for 60 C. for 2 hours to obtain solution B. A fiber treating solution is prepared by adding solution B to the solution A, and then fixed onto clothes.

In the present invention, as to the natural moisturizing factor components, for example, an extract of animal protein hydrolysate having a molecular weight of 5,000 to 100,000 is used as amino acids and peptides, chitosan is used as a glucosamine, chitosan lactate is used as a lactate, and Na, etc. can be included by the neutralization with an alkaline of the acid used in the protein hydrolysis. About 80% of the natural moisturizing factor components can be fixed onto fibers by applying these components without having to use a synthetic resin binder, if possible.

Animal protein hydrolysates are highly effective to physiologically improve immunity and rough and dry skin since they contain amino acids such as arginine, lysine, histidine, leucine, phenylalanine, glycine, valine, proline, glutamic acid, and aspartic acid.

In the present invention, examples of effective fiber materials include cotton, rayon, acetate, linen, cupra rayon, acryl, and nylon. Urethane binders can be supplementarily used in combination for polyester fibers, polypropylene fibers, or the like. Fiber treating agents of the present invention can be applied onto fibers singly or in combination with conventional fiber finishing agents.

A 100% cotton knitted fabric was treated with a fiber treating agent of the present invention and the amino acid contents of the treated fiber was analyzed before and after washing at the Japan Food Analysis Center in order to prove washing durability. Results are shown in Table 2 below.

Table 2 Amino acid contents of the cotton fabric treated in Example 1 (mg/100 g)

TABLE 2

Amino acid contents of the cotton fabric treated in Example 1 (mg/100 g)

| Amino acid | No washing | Washed 10 times | Washed 50 times |
| --- | --- | --- | --- |
| Arginine | 12 | 7 | 6 |
| Aspartic acid | 33 | 18 | 15 |
| Threonine | 19 | 12 | 10 |
| Phenylalanine | 11 | 10 | 9 |
| Leucine | 21 | 18 | 15 |
| Isoleucine | 11 | 10 | 9 |
| Alanine | 17 | 13 | 11 |
| Valine | 17 | 12 | 10 |
| Glycine | 17 | 9 | 7 |
| Glutamic acid | 24 | 18 | 15 |
| Serine | 36 | 13 | 10 |
| Lysine | 5 | 3 | 2 |
| Histidine | 3 | 1 | 1 |

In Example 1 described below, a knitted cotton fabric was treated with a sericin hydrolysate. Amino acids of natural moisturizing factor components remained on the fabric even after washing 50 times, which proved excellent washing durability. A high content of aspartic acid is particularly characteristic to the sericin-derived component. As shown in the results after 10 and 50 washings, the contents of natural moisturizing factor components decreased with the number of washings; however, the moisture-retaining effect was satisfactorily maintained as shown in Table 3 in Example 1 and Table 4 in Example 4, below. Thus, an appropriate decrease in contents of the natural moisturizing factor components is essential since a small amount of released components acts on the skin to exhibit the resulting physiological protective effects.

In the present invention, it is preferable to combine allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, obaku (bark of Phellodendron amurense) extract component, or the like with the abovementioned fiber treating agents, in order to further improve the effect of preventing rough and dry skin. Further, in the case of synthetic fabrics for panty hose, binders such as urethane binders can be added in a small amount so as not to interfere with the physiological skin protecting function and comfortable feel of fabrics.

According to the present invention, woven fabrics, webs, or non-woven fabrics for underwear, bath robes, towels, bed sheets, socks and stockings, panty hose, fiber products for medical use, or the like are treated with the abovementioned treating solution containing the natural moisturizing factor components to provide the fabrics with a gentle and soft and supple feel to the skin and physiological skin protecting effects for preventing rough, dry and itchy skin, and improving eczema or the like.

EXAMPLE 1

Preparation of solution A: A chitosan lactate solution was obtained by mixing 2% by weight chitosan, 2% by weight lactic acid and 96% by weight water and reacting the admixture at 50 C. for 40 minutes. Separately, 100 g of 10% hydrochloric acid were added to 100 g of a sericin solution extracted from silk, the admixture was hydrolyzed at 50 C. for 1 hour, the resulting hydrolysate was neutralized with sodium hydroxide and then filtered using a filter paper, and the filtrate was fractionated by gel filtration. Then, a protein fraction having a molecular weight of 10,000 to 20,000 was recovered and concentrated to obtain a solution containing 2% sericin hydrolysate component.

Solution A was obtained by mixing 60 parts of the abovementioned chitosan lactate solution and 40 parts of the abovementioned sericin hydrolysate solution and stirring the admixture at 60 C. for 2 hours.

Preparation of solution B: Solution B was obtained by mixing 40 parts of YSB-TX (a 30% guanidine ammonium salt solution; a product of SK, Korea) and 20 parts of cetyl trimethylammonium salt (a 30% solution), as quaternary ammonium salts, and 40 parts of the abovementioned sericin hydrolysate component solution and stirring the admixture at 60 C. for 2 hours.

Preparation of fiber treating solution: Equal amounts of solution A and solution B were mixed, stirred and further diluted 10 times with purified water to obtain the fiber treating solution.

The treating solution thus obtained was applied by soaking using a mangle to a 100% cotton knitted fabric for underwear in an amount of 200% by weight of the fabric, after which the fabric was dried at 100 C. The washing durability of amino acids fixed on the treated cotton fabric was revealed to be excellent as shown in Table 2 above.

Furthermore, long sleeve undershirts having different fabric materials on the right and left side were sewn using the fabric treated as in Example 1 for the left side and a conventional ordinary cotton fabric as a control for the right side. The undershirts thus sewed were subjected to a wearing test by patients having atopic dermatitis. Results are shown in Table 3.

TABLE 3

| | Degree of improvement | | | |
|---|---|---|---|---|
| | Excellent | Moderate | Slight | None |
| Left: treated fabric | 3 | 4 | 2 | 1 |
| Right: untreated fabric | 0 | 1 | 4 | 5 |

Ten atopic dermatitis patients of age 15 to 38 having eczema on the chest, back and upper arms were subjected to the wearing test. The dermatitis was severe in 3 patients and moderate in 7 patients. The wearing test was carried out for 6 to 8 weeks. The shirts were washed at the end of each day using a home electric washing machine.

General conditions were compared with those at the starting day to evaluate the degree of improvement. According to self-evaluations, itching on the right side of the body (with fabric treated according to the present invention) was reduced. Thus, underwear treated with the solution of the present invention is considered to be highly safe for wear by patients with atopic dermatitis.

EXAMPLE 2

Preparation of solution A: A chitosan lactate solution was obtained by mixing 2% by weight chitosan, 2% by weight lactic acid and 96% by weight water and reacting the admixture at 50 C. for 40 minutes. Separately, 100 g of 10% hydrochloric acid were added to 100 g of a sericin solution extracted from silk, the admixture was hydrolyzed at 50 C. for 1 hour, the resulting hydrolysate was neutralized with sodium hydroxide and then filtered using a filter paper, and the filtrate was fractionated by gel filtration. Then, a protein fraction having a molecular weight of 10,000 to 20,000 was recovered and concentrated to obtain a solution containing 2% sericin hydrolysate component.

Solution A was obtained by mixing 60 parts of the abovementioned chitosan lactate solution and 40 parts of the abovementioned sericin hydrolysate solution and stirring the admixture at 60 C. for 2 hours. Preparation of solution B: Solution B was obtained by mixing a solution composed of 40 parts of palmalkyl trimethylammonium salts (a 30% solution) as a quaternary ammonium salt and 5 parts of trimethyl glycine with 40 parts of the abovementioned sericin hydrolysate component solution and 15 parts of water and stirring the admixture at 60 C. for 2 hours. Preparation of treating solution: Equal amounts of solution A and solution B were mixed, and further diluted 10 times with purified water to obtain the treating solution.

The treating solution thus obtained was applied by soaking using a mangle to a 100% cotton fabric for towels in an amount of 200% by weight of the fabric, after which the fabric was dried at 120 C. to obtain a material having soft and comfortable feel. The soft and supple feel of the treated fabric did not change after washing 50 times and thus the washing durability was confirmed.

Furthermore, the water absorbing property was excellent because of the moisture-retaining effect. In order to evaluate antimicrobial activity, changes in bacterial counts were measured by culturing *Staphylococcus aureus* JFO12732 for 18 hours.

As shown in the results in Table 4, excellent antibacterial activity was observed even after washing 50 times.

TABLE 4

Results of antibacterial test

| | Number of washings | Bacterial count of inoculum | Bacterial count after 18 hrs |
|---|---|---|---|
| Towels treated in Example 2 | Unwashed | $4 \times 10^8$ | Less than $10^2$ |
| | Washed 10 times | $4 \times 10^8$ | Less than $10^2$ |
| | Washed 50 times | $4 \times 10^8$ | Less than $10^2$ |
| Untreated towels (control) | Unwashed | $4 \times 10^8$ | $3 \times 10^8$ |
| | Washed 10 times | $4 \times 10^8$ | $5 \times 10^8$ |

EXAMPLE 3

Preparation of solution A: A chitosan lactate solution was obtained by mixing 2% by weight chitosan, 2% by weight lactic acid and 96% by weight water and reacting the admixture at 60 C. for 40 minutes. Solution A was obtained by mixing 60 parts of the resulting chitosan lactate solution and 40 parts of an extract having a molecular weight of 10,000 to 20,000 derived from collagen (a 2% solution) and stirring the admixture at 60 C. for 2 hours. Preparation of solution B: First, 20 parts of trimethylglycine and lauryl trimethylammonium salt (a 3% solution), as quaternary ammonium salts, and 40 parts of the abovementioned collagen extract solution were mixed and stirred at 60 C. for 2 hours, and 20 parts of UPM-Z12HN (a trade name, a urethane binder manufactured by Teikoku Kasei KK; at a concentration of 30%) was supplementarily mixed with this admixture to obtain solution B.

Equal amounts of solution A and solution B were mixed, stirred and further diluted 10 times with purified water to obtain the fiber treating solution.

The treating solution thus obtained was applied to nylon panty hose by soaking, and then dried at 100 C. The treated panty hose were confirmed to exhibit physiological skin protection effects providing a smooth, soft and supple feel, and much better wear feeling because of its moisture retaining property as compared to conventional products.

Effectiveness of the Invention

As mentioned above, a fiber treating agent of the present invention can restore the skin barrier function and improve the moisture-retaining function of the horny layer by fixing high contents of the natural moisturizing factor components onto fibers, unlike moisture-retaining agents which are conventionally used for cosmetics or the like. The present invention can provide underwear having a gentle, soft and supple feel to the skin and protective effects by fixing the natural moisturizing factor components onto fibers without having to use a synthetic resin binder, if possible.

What is claimed is:

1. A fiber treating agent having physiological skin protecting effects, comprised of an animal protein hydrolysate, chitosan lactate and one or more kinds of quaternary ammonium salts, and characterized in that said agent fixes natural skin moisturizing factor components onto clothes.

2. A fiber treating agent as claimed in claim 1, characterized in that it comprises solution A prepared by mixing and heating 1 part by weight of an animal protein hydrolysate and 1 to 3 parts by weight of chitosan lactate and solution B prepared by mixing and heating 1 part of an animal protein hydrolysate by weight and 1 to 3 parts by weight of quaternary ammonium salts.

3. A fiber treating agent as claimed in claim 1, wherein said animal protein hydrolysate is an extract of natural collagen or atherocollagen hydrolysate extracted from animal skin bones, having a molecular weight of 5,000 to 100,000, or an extract of sericin or fibroin hydrolysate having a molecular weight of 5,000 to 100,000.

4. A fiber treating agent as claimed in claim 2, wherein said animal protein hydrolysate is an extract of natural collagen or atherocollagen hydrolysate extracted from animal skin bones, having a molecular weight of 5,000 to 100,000, or an extract of sericin or fibroin hydrolysate having a molecular weight of 5,000 to 100,000.

5. A fiber treating agent as claimed in claim 1, wherein said quaternary ammonium salts are at least one or more kinds of salts selected from the group consisting of alkyl trimethylammonium salts, betaine ammonium salts, and guanidine ammonium salts.

6. A fiber treating agent as claimed in claim 2, wherein said quaternary ammonium salts are at least one or more kinds of salts selected from the group consisting of alkyl trimethylammonium salts, betaine ammonium salts, and guanidine ammonium salts.

7. A fiber treating agent as claimed in claim 3, wherein said quaternary ammonium salts are at least one or more kinds of salts selected from the group consisting of alkyl trimethylammonium salts, betaine ammonium salts, and guanidine ammonium salts.

8. A fiber treating agent as claimed in claim 4, wherein said quaternary ammonium salts are at least one or more kinds of salts selected from the group consisting of alkyl trimethylammonium salts, betaine ammonium salts, and guanidine ammonium salts.

9. A fiber treating agent as claimed in claim 1, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

10. A fiber treating agent as claimed in claim 2, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

11. A fiber treating agent as claimed in claim 3, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

12. A fiber treating agent as claimed in claim 4, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

13. A fiber treating agent as claimed in claim 5, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

14. A fiber treating agent as claimed in claim 6, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

15. A fiber treating agent as claimed in claim 7, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

16. A fiber treating agent as claimed in claim 8, characterized in that it is further combined with allantoin, glytyl retinoate, shikon (root of Lithospermum erythrorhizon) extract component, aloe extract component, gardenia extract component, citric acid, tartaric acid, hamamelis extract component, yarrow extract component, saxifrage extract component, magwort extract component, carrot extract component, sponge gourd extract component, horse chestnut extract component, or obaku (bark of Phellodendron amurense) extract component.

17. A method of treating fibers comprising soaking the fibers using a fiber treating agent as claimed in claim 1, characterized in that it comprises solution A prepared by mixing and heating 1 part by weight of an animal protein hydrolysate and 1 to 3 parts by weight of chitosan lactate and solution B prepared by mixing and heating 1 part by weight of an animal protein hydrolysate by weight and 1 to 3 parts by weight of quaternary ammonium salts.

18. A method of treating fibers as claimed in claim 17, wherein said fibers are woven fabrics, webs, non-woven fabrics for underwear, bath robes, towels, socks and stockings, or fiber products for medical use, and are provided with a gentle and soft feel to the skin, and permanent physiological skin protecting effects for preventing rough, dry and itchy skin and improving immunity.

* * * * *